United States Patent [19]

Baldwin et al.

[11] 4,169,835

[45] Oct. 2, 1979

[54] 2-AMINO PROPANOL ISOTHIOZOL-3-ONES

[75] Inventors: John J. Baldwin; Gerald S. Ponticello, both of Lansdale, Pa.

[73] Assignee: Merck & Co., Inc., Rahway, N.J.

[21] Appl. No.: 883,568

[22] Filed: Mar. 6, 1978

Related U.S. Application Data

[62] Division of Ser. No. 792,743, May 2, 1978, Pat. No. 4,119,718.

[51] Int. Cl.² ............................................ C07D 275/02
[52] U.S. Cl. .................................... 548/213; 544/133; 544/367; 546/209
[58] Field of Search ......................... 260/302 S, 302 A

[56] References Cited

FOREIGN PATENT DOCUMENTS 2043209  4/1970  Fed. Rep. of Germany .
1013224  12/1965  United Kingdom ..................... 546/176

Primary Examiner—Donald G. Daus
Assistant Examiner—Lisa Jones
Attorney, Agent, or Firm—Daniel T. Szura; Harry E. Westlake, Jr.

[57] ABSTRACT

Novel isothiazoles having a 3-amino-2-OR-propoxy or -propyl substituent are disclosed. The isothiazoles have pharmaceutical activity.

3 Claims, No Drawings

2-AMINO PROPANOL ISOTHIOZOL-3-ONES

This is a division of application Ser. No. 792,743 filed May 2, 1977 now U.S. Pat. No. 4,119,718.

BACKGROUND OF THE DISCLOSURE

The present invention involves novel 3-amino-2OR-propoxy or-propyl substituted isothiazoles which have pharmaceutical activity e.g. β-adrenergic blockade.

Thiazoles having an aminohydroxypropoxy substituent, are known and are taught to have β-adrenergic activity. See U.S. Pat. No. 3,850,945, U.S. Pat. No. 3,850,946, U.S. Pat. No. 3,850,947 U.S. Pat. No. 3,897,441 and U.S. Pat. No. 3,897,442. No isothiazoles are suggested.

Novel isothiazole compounds having a 3-amino-2-OR-propoxy or-propyl substituent have been discovered. These isothiazoles have pharmaceutical activity.

SUMMARY OF THE INVENTION

Isothiazoles having a 3-amino-3-OR-propoxy or-propyl substituent and their pharmaceutical use.

DESCRIPTION OF THE PREFERRED EMBODIMENTS

An embodiment of the present invention is compounds having the formula

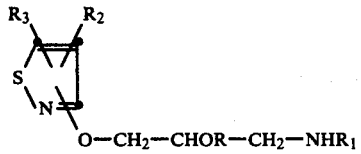

and pharmaceutically acceptable salts thereof wherein

R is hydrogen or $C_2$-$C_{12}$acyl, $R_1$ is $C_1$-$C_{12}$alkyl, $R_2$ is H, Cl, Br, F, CN, -$NH_2$, —$COOR_4$ wherein $R_4$ is H $C_1$-$C_6$alkyl or $C_6$-$C_{12}$ carbocyclic aryl, —$CONR_5R_6$ wherein $R_5$ and $R_6$ when separate, are H or $C_1$-$C_6$alkyl and when joined, are —$CH_2$—$(CH_2)_3$ —$CH_2$, —$CH_2$—$CH_2$—O—$CH_2$—$CH_2$—, —$CH_2$—$CH_2$—NH—$CH_2$—$CH_2$—, or —$CH_2$—$CH_2$—N($CH_3$)—$CH_2$—$CH_2$—, —$C_1$-$C_6$alkylthio, —$C_1$-$C_6$ alkylsulfinyl or —$C_1$-$C_6$alkylsulfonyl and $R_3$ is H, $C_1$-$C_6$ alkylthio, $C_1$-$C_6$ alkylsulfinyl or $C_1$-$C_6$ alkylsulfonyl.

The pharmaceutically acceptable salts are the acid addition salts of the formula I free base. Suitable acids include organic as well as inorganic acids. Examples of useful organic acids are carboxylic acids such as acetic acid, pamoic acid, maleic acid, succinic acid, citric acid, tartaric acid, oxalic acid, malic acid, pivalic acid, heptanoic acid, lauric acid, propanoic acid, pelargonic acid, oleic acid and the like, and non-carboxylic acids such as isethionic acid. Examples of useful inorganic acids are the hydrogen halides i.e. HCl, HBr, HI, phosphoric acid, sulfuric acid, and the like. The hydrohalide salts, especially the hydrochlorides and maleic acids, especially the hydrogen maleate, are preferred.

R may be hydrogen or $C_{2-12}$ acyl. The $C_{2-12}$ acyl groups include alkanoyl groups such as acetyl, pivaloly, dodecanoyl, hexanoyl, succinoyl and the like—and carbocyclic aroyl groups such as benzoyl, 1- or 2-naphthoyl, p-methylbenzoyl, p-phenylbenzoyl and the like. The $C_2$-$C_6$ alkanoyl and benzoyl groups are preferred acyl groups. Hydrogen is a most preferred R group.

The $R_1$ substituent includes $C_1$-$C_{12}$alkyl groups and preferably the $C_1$-$C_6$alkyl groups. The alkyl groups are exemplified by methyl, $C_{12}H_{25}$, hexyl, 2-ethylhexyl, isopropyl, sec-butyl, heptyl nd the like. The $C_{3-4}$ branched chain alkyl $R_1$ groups are more preferred, with t-butyl being a most preferred group.

The $R_2$ substituent includes hydrogen, Cl, Br, F, —CN, —$NH_2$, the carboxy group and ester and amide derivatives thereof, the $C_1$-$C_6$alkylthio and sulfinyl and sulfonyl derivatives thereof. The ester groups are $C_1$-$C_6$-alkylester exemplified by —$COOCH_3$, —$COOC_6H_{13}$, —$COOCH(CH_3)_2$, —$COOC_2H_5$ and the like and $C_6$-$C_{12}$ arylester, preferably carbocyclic aryl, exemplified by $C_6H_5$—OOC, p—$CH_3$—$C_6H_5$—OOC—, $C_6H_5$—$C_6H_5$—OOC—, $C_{10}H_8$—OOC— and the like. The amide groups include —$CONH_2$, $C_1$-$C_6$ substituted amide groups such as —$CON(CH_3)_2$, —$CON(C_6H_{13})_2$, —$CONHC_2H_5$, —CON (sec. butyl)$_2$ and the like and carbonyl heterocyclic groups such as

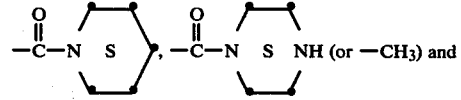

, —C—N S NH (or —$CH_3$) and

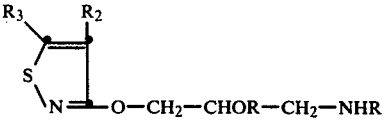

The $C_1$-$C_6$ alkyl-thio, -sulfinyl and -sulfonyl groups are exemplified by $CH_3$—S—, $C_6H_{13}$—SO—, $(CH_3)_3C$—S—, $(CH_3)_2CH$—SO—, $CH_3SO_2$—, $C_2H_5$—$SO_2$, $C_6H_{13}$—S; $C_5H_{11}$—SO—, sec.-butyl-$SO_2$ and the like. Of the $R_2$ groups CN and Br are preferred.

$R_3$ includes $C_{1-6}$alkylthio, -sulfinyl and sulfonyl groups such as —S—$CH_3$, —S—$C_6H_{13}$, —S—$C(CH_3)_3$, —S—$C_2H_5$, —$SO_2$—$CH_3$, —$SO_2$—$CH(CH_3)_2$, —$SO_2$—$C_5H_{11}$, —SO—$C_4H_9$, —SO-sec. butyl and the like. Of the alkylthio groups methylthio is preferred.

The formula I compounds have one chiral center which confers optical activity. The optical isomers are designated conventionally as L and D, l and d, + and —, S and R or by combinations of these symbols. Where the formula or compound name herein carries no specific designation, the formula or name includes the individual isomers, the mixtures thereof and racemates.

The formula I compounds which are preferred have the formula

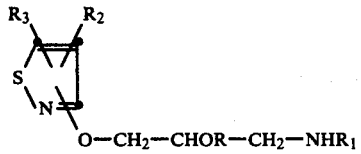

Formula II compounds where $R_3$ is H or $C_1$-$C_6$ alkylthio, preferably $CH_3$—S— and $R_2$ is H, CN, Cl, Br or F, preferably CN, are especially preferred; and where R is hydrogen and $R_1$ is $C_1$-$C_6$alkyl, preferably $C_3$-$C_4$ branched alkyl, the compounds are particularly preferred.

The isothiazole compounds which are more preferred have the formula

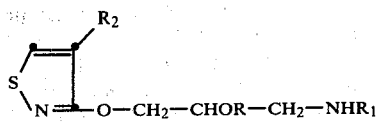

III

Where $R_2$ is (a) other than hydrogen, (b) H, CN, Br, Cl or F or (c) Cl, Br, F or CN, formula III compounds are especially preferred—and the compounds are particularly preferred where R is hydrogen, $R_1$ is $C_1$-$C_6$alkyl, preferably $C_3$-$C_4$ branched alkyl and $R_2$ is Br or CN.

The isothiazoles of the present invention have $\beta$-adrenergic blocking activity. This was determined in an in-vivo test using dogs as the test animals. In this test, representative isothiazole compounds, were found to counteract the $\beta$-adrenergic stimulating effect of isoproterenol.

The compounds of formula III where $R_2$ is other than hydrogen also have antihypertensive effect of immediate onset. When representative compounds were administered (orally or intraperitoneally) to a spontaneously hypertensive (SH) rat, an immediate reduction in arterial blood pressure was observed.

The present isothiazoles also show random vasodilator activity.

The present isothiazole compounds will effect $\beta$-adrenergic blockade in humans. This $\beta$-adrenergic blocking effect is useful in the therapeutic treatment of various cardiovascular conditions such as angina pectoris, arrhythmia etc. In administering these formula I compounds for their $\beta$-adrenergic blocking effect, the daily dosage may range from about 1.5 mg. to about 3000 mg. Preferred daily dosages are about 6.5 mg. to about 200 mg. Conventional dosage forms suitable for oral as well as parenteral, e.g. intravenous, intraperitoneal etc., administration are used. Oral dosage forms include tablets, capsules, troches, liquid formulations e.g. solutions, emulsions elixirs etc.—parenteral dosage forms include liquid formulations especially solutions. The compositions are prepared using conventional procedures and compounding ingredients such as starch, sterile water, flavoring additives, antioxidants, binders, vegetable oils, sweetening agents, glycerine and the like.

The compounds of formula III wherein $R_2$ is other than hydrogen are also useful for treating hypertensive humans. The daily dosage of these antihypertensive compounds may vary from about 40 mg. to about 3000 mg. Preferred daily dosages are about 100 mg. to about 1500 mg. Again, the compounds are administered in dosage forms suitable for oral or parenteral administration. Oral dosage forms include tablets, capsules, troached, liquid formulations e.g. solution, emulsion etc.—the parenteral dosage forms are generally liquid forms such as solutions or emulsions. Conventional pharmaceutical composition preparation procedures and compounding ingredients (diluents, excipents etc.) are utilized.

The present isothiazoles can be prepared by any convenient process.

One such process involves the coupling of a suitably substituted isothiazole with a suitably substituted oxazolidine and hydrolyzing the reaction product obtained. This process is illustrated by the following set of reaction equations:

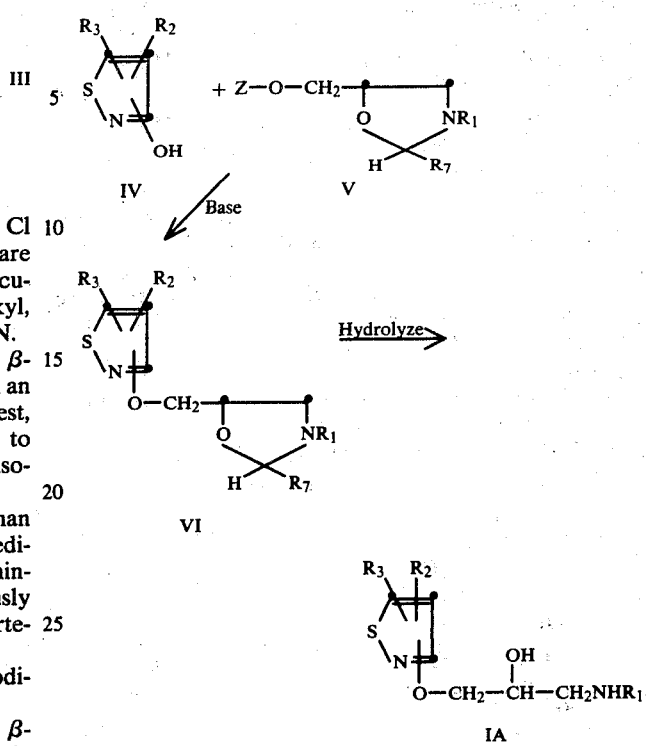

Z is an alkyl or arylsulfonyl group. Examples of sulfonyl groups are $CH_3$—$SO_2$—, $C_6H_5$—$SO_2$—, $NO_2$—$C_6H_5$—$SO_2$—, p—$CH_3$—$C_6H_4$—$SO_2$—, mesitylene—$SO_2$—$CH_3O$—$C_6H_4$—$SO_2$—, trichlorobenzene—$SO_2$—, $C_{16}H_{33}$—$SO_2$—and the like. Suitable bases are alkali metal bases such as $K_2CO_3$, K—O—$C(CH_3)_3$, NaH, organolithiums e.g. phenyllithium, n-butyllithium, lithium diisopropyl amide and the like.

$R_7$ is hydrogen or other $C_1$-$C_{12}$ alkyl or $C_6$-$C_{12}$ carbocyclic aryl residue of any suitable aldehyde

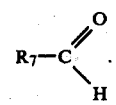

Examples of suitable aldehydes are the aryl aldehydes such as benzaldehyde, naphthaldehyde 4-phenylbenzaldehyde, bromobenzaldehyde, tolualdehyde, mesitaldehyde and the like, or an alkanal such as acetaldehyde, butraldehyde

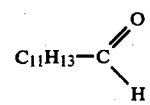

and the like. The process for preparing oxazolidines where Z is hydrogen (and a related coupling reaction) is disclosed in U.S. Pat. No. 3,718,647 and U.S. Pat. No. 3,657,237 and to the extent necessary the pertinent disclosure is incorporated herein be reference. Some isothiazole intermediates of formula II are disclosed in German OLS No. 2,043,209 and to the extent necessary this disclosure is also incorporated herein by reference.

The coupling reaction can be carried out at temperatures ranging from about 0° to about 130° C. A temperature range of about 50° to about 130° C. is preferred. The reaction is generally carried out in a solvent. Any suitable solvent may be used. Examples of useful solvents are dimethylformamide, dimethylsulfoxide, hexamethylphosphoramide, tert. butanol, alkanols, dioxane, toluene, acetone and the like. The hydrolysis is carried out using a conventional acid system e.g. by treatment with a solution of any suitable acid such as HCl, $H_2SO_4$, $CH_3COOH$ and the like. The hydrolysis product can be directly obtained as the salt of the acid used for the hydrolysis. Ordinarily, the product IA is recovered as the free base after conventional neutralization of the salt.

The coupling reaction is ordinarily carried out at atmospheric pressure. Higher pressures may be used if desired.

When a racemic oxazolidine (formula V) is used as a reactant, the product is obtained as a racemate. The racemate may be separated into its individual enantiomers by conventional resolution techniques.

When $R_7$ in the oxazolidine (e.g. formulae V or VI) is other than hydrogen, in addition to the chiral center at oxazolidine position 5 there is a second chiral center at position 2. However, whenever an oxazolidine is designated e.g. as (S), (R) or (R,S), this designation refers only to the optical configuration around the carbon atom at the 5 position.

By using a single optical isomer of the formula V oxazolidine in the above reaction the isothiazole product (IA) may be obtained directly as a single enantiomer. This provides a convenient way for directly preparing individual isomers of the present isothiazoles.

Isothiazoles represented by formula I wherein R is other than hydrogen are conveniently prepared by treating the corresponding isothiazole where R is hydrogen with an appropriate acylating agent such as an acyl halide, e.g. undecanoyl chloride, pivaloyl chloride, benzoylchloride, p-methoxybenzoyl chloride, an anhydride e.g. acetic anhydride and the like. The reaction is illustrated by the following equation:

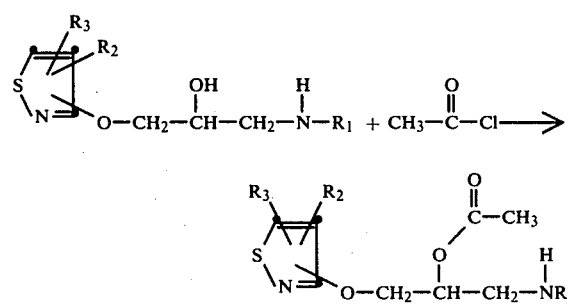

The compounds of the present invention also include the pharmaceutically acceptable salt of the novel isothiazoles. These salts are conveniently prepared e.g. by treating the isothiazole with an appropriate amount of a useful acid, generally in a suitable solvent.

Another process for preparing the isothiazoles having a cyano substituent is by halogen displacement as illustrated by the following equation:

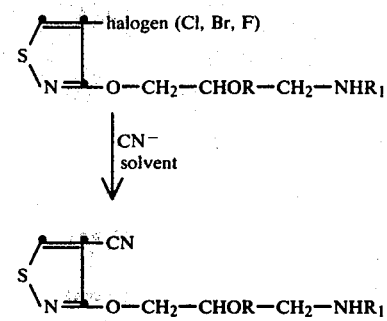

The $CN^-$ supplying reagent may be any suitable metal salt such as CuCN, AgCN, etc. Solvents which may be used are examplified by dimethylformamide, pyridine, 2,4-lutidine and the like. The reaction is generally carried out at elevated temperature, preferably in the 100°–180° C. range.

Additional processes for preparing isothiazoles with certain other substituents are illustrated by the following equation sequences. Conventional reaction conditions are employed. The desired other substituent is underlined. The symbol L represents the $-CH_2-CHOR-CH_2-NR_1$ group.

Sequence 1

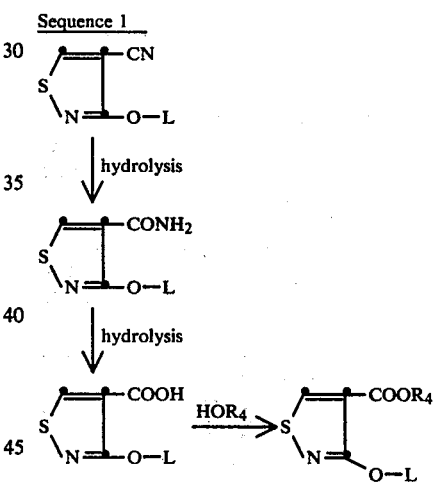

Sequence 2

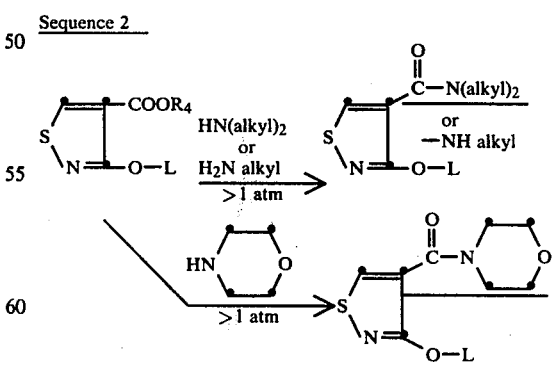

Sequence 3

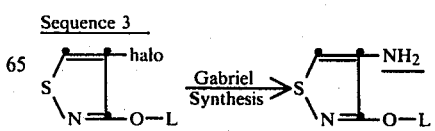

The isothiazoles having an alkylsulfinyl or alkylsulfonyl substituent are prepared by oxidizing the corresponding $C_1$-$C_6$ alkylthio containing compound. Any suitable oxidizing agent, e.g. $H_2O_2$, may be used. The following equation illustrates the reaction

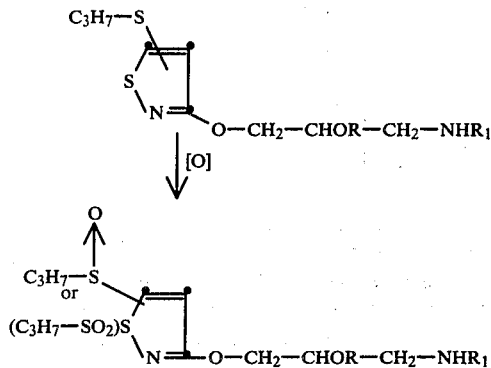

Another embodiment of the present invention is an isothiazole-3-one of the formula

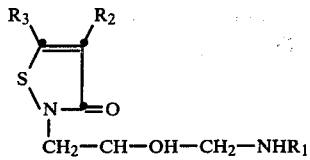

VII and pharmaceutically acceptable salts thereof wherein $R_1$, $R_2$ and $R_3$ are as defined above. Compounds of formula VII where $R_2$ is H, Cl, Br, F or CN and $R_3$ is H or $C_1$-$C_6$ alkyl are preferred.

The compounds of formula VII are β-adrenergic blocking agents. A representative compound where $R_2$ and $R_3$ were other than hydrogen also exhibited antihypertensive activity when administered intraperitoneally in the SH rat.

The compounds of formula VII are obtained by alkylation of formula IV compound with formula V compound on nitrogen followed by acid hydrolysis of the oxazolidine intermediate having the formula

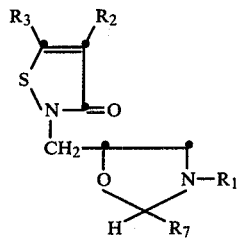

VIII

The following examples illustrate the preparation of representative compounds of the present invention. All temperatures are in ° C.

EXAMPLE 1

(S) 3-(3-tert. Butylamino-2-hydroxypropoxy)isothiazole maleate salt

Into a dry flask under $N_2$ is added 3-hydroxyisothiazole (0.1 m), DMF (250 ml.), and NaH (50% mineral oil, 5.0 g., 0.104 m). After stirring for 15 minutes, a solution of the tosylate of (S) 2-phenyl-3-tert. butylamino-5-hydroxymethyloxazolidine (0.1 m.) in dimethylformamide (DMF) (150 ml.) is added and the solution heated on a steam bath with stirring. After 15 hours, the solution is cooled to 0°-10°, poured into $H_2O$ (1.5 l) and extracted with ether (5×30 ml.). The organic layer is washed with $H_2O$ (2×400 ml.) and 1N HCl (3×200 ml.). The acid layer is heated on a steam bath for 15 minutes, cooled to 0°-4° and extracted with ether (2×300 ml.). The aqueous layer is neutralized with saturated $Na_2CO_3$ solution and extracted with $CH_2Cl_2$ (4×100 ml.). The organic layer is dried over $Na_2SO_4$, filtered and concentrated to dryness. The residue is treated with maleic acid (10.5 g.) in isopropanol (IPA) to yield 19.8 g. (57%) of 3-(3-tert. butylamino-2-hydroxypropoxy)isothiazole hydrogen maleate salt m.p. 187°-88°.

The corresponding hydrochloride is prepared by treating the residue with HCl instead of maleic acid.

EXAMPLE 2

(S) 4-Bromo-3-(3-tert, butylamino-2-hydroxypropoxy) isothiazole hydrogen maleate salt Into a dry flask under $N_2$ is added 4-bromo-3-hydroxy isothiazole hydrobromide (3.3 g., 0.013 m), DMF (40 ml.), and NaH (50% mineral oil, 1.2 g., 0.025 m). After stirring for 15 minutes, a solution of the tosylate of (S) 2-phenyl-3-tert. butylamino-5-hydroxymethyloxazolidine (0.013 m.) in DMF (20 ml.) is added and the solution heated at 80°. After 15 hours, the solution is cooled to 0°-10°, poured into $H_2O$ (300 ml.) and extracted with ether (3×100 ml.). The organic layer is washed with $H_2O$ (2×100 ml.) and 1N HCl (4×60 ml.). The acid layer is heated on a steam bath for ½ hour, cooled to 0°-4° and extracted with ether (2×100 ml.). The aqueous layer is neutralized with saturated $Na_2CO_3$ and extracted with $CHCl_3$ (3×200 ml.). The organic layer is dried over $Na_2SO_4$, filtered and concentrated to dryness. The residue is chromatographed on silica gel 60 and the product eluted with $CHCl_3$ saturated with aqueous $NH_3$. The crude product is crystallized with maleic acid in IPA-$ET_2O$ to yield 1.5 g. (45%) of (S) 4-bromo-3-(3tert.-butylamino-2hydroxypropoxy) isothiazole hydrogen maleate salt, m.p. 162°-64°.

(S) 4-Amino-3(3-tert. butylamino-2-hydroxypropoxy) isothiazole is obtained from (S) 4-bromo-3-(3-tert. butylamino-2-hydroxypropoxy)isothiazole via the Gabriel synthesis.

EXAMPLE 3

(S) 4-Cyano-3-(3tert. butylamino-2-hydroxypropoxy) isothiazole hydrogen maleate salt Into a flask under $N_2$ is placed (S) 4-bromo-3-(3-tert. butylamino-2-hydroxypropoxy)isothiazole (3.0 g., 0.013 m), CuCN (4.3 g., 0.076 m) and DMF (20 ml.). The solution is heated to reflux with stirring for 1 hour. After cooling, a solution of NaCN (2.7 g.) in $H_2O$ (9 ml.) is added, the solution cooled to 25°, and a second portion of NaCN (5.7 g.) in $H_2O$ (16 ml.) is then added. The layers are separated and the aqueous layer further extracted with $Et_2O$ (4×50 ml.). The organic layers are washed with 10% NaCN (2×50 ml.), $H_2O$ (50 ml.), dried over $Na_2SO_4$, filtered and concentrated to dryness. The residue is chromatographed on silica gel 60 and the product eluted with $CHCl_3$ saturated with aqueous $NH_3$. The crude product is further purified by thick layer chromatography on 2000 micron silica gel plates eluting with $CHCl_3$ saturated with aqueous $NH_3$ and then crystallized with maleic acid in IPA/$Et_2O$ to yield 0.3 g. (6%) of (S) 4-cyano-3-(3-tert. butylamino-2-hydroxypropoxy) isothiazole hydrogen maleate salt, m.p. 171°-172° C.

The corresponding (a) 4—CONH$_2$ or (b) 4—COOH—3-(3-tert. butylamino-2-hydroxypropoxy)isothiazole is obtained from the stepwise hydrolysis of the Example 3 product.

By substituting (S,R) 4-bromo-3-(3-isopropylamino-2-hydroxypropoxy)isothiazole for the (S) 4-bromo-3-(3-tert.-butylamino-2-hydroxypropoxy)isothiazole in Example 3, (S,R) 4-cyano-3-(3-isopropylamino-2-hydroxypropoxy)isothiazole hydrogen maleate salts is obtained.

EXAMPLE 4

(S) 4-Cyano-3-(3tert. butylamino-2-hydroxypropoxy)-5-methylthioisothiazole hydrogen maleate salt hemihydrate To a stirred solution of (S) 2-phenyl-3-tert. butylamino-5-hydroxymethyloxazolidine (12.5 g., 0.053 m.) and dry pyridine (10 ml.) is added portionwise p-toluenesulfonyl chloride (10 g., 0.053 m.), while maintaining the temperature of the reaction below 30°. After the addition, the mixture is stirred at room temperature for 3 hours. To the solid mixture is added a solution of K$_2$CO$_3$ (7.0 g., 0.05 m.) in H$_2$O (50 ml.) and the mixture extracted with CHCl$_3$ (3×50 ml.). The organic layer is dried over Na$_2$SO$_4$, filtered and concentrated to dryness below 50° to yield the tosylate of (S) 2-phenyl-3-tert. butylamino-5-hydroxymethyloxazolidine which is used in the next step without further purification.

Into a dry flask under N$_2$ is added 4-cyano-3-hydroxy-5-methylthioisothiazole (8.6 g., 0.05 m.), DMF (120 ml.) and NaH (50% mineral oil, 2.5 g., 0.052 m.). After stirring at room temperature for 15 minutes, the tosylate of (S) 2-phenyl-3-tert. butylamino-5-hydroxymethyloxazolidine (0.05 m.) in DMF (80 ml.) is added and the solution heated at 80° C. with stirring. After 15 hours, the solution is cooled to 0°-10°, poured into H$_2$O (600 ml.) and extracted with ether (4×100 ml.). The organic layer is washed with H$_2$O (2×100 ml.) and 1N HCl (3×100 ml.). The acid layer is poured into NaOAc.3H$_2$O (41 g., 0.3 m.) and the solution stirred at room temperature. After 5 hours, the solution is extracted with ether (2×100 ml.). The aqueous layer is neutralized with saturated Na$_2$CO$_3$ and extracted with CHCl$_3$ (4×150 ml.). The organic layer is dried over Na$_2$SO$_4$, filtered and concentrated to dryness. The residue is chromatographed on silica gel 60 and the product eluted with CHCl$_3$ saturated with ammonia. There is obtained 6.3 g. (42%) of (S) 4-cyano-3-(tert.-butylamino-2-hydroxypropoxy)-5-methylthioisothiazole, which on treatment with maleic yields the (S) 4-cyano-3-(3-tert. butylamino-2-hydroxypropoxy(-5-methylthioisothiazole hydrogen maleate salt hemihydrate, m.p. 199°-200° C.

A second more polar compound is isolated from the chromatography. The crude compound is crystallized from maleic acid (0.5 g. 0 in IPA to yield 0.9 g. (6%) of (S) 4-cyano-5-methylthio-2-(3-tert. butylamino-2-hydroxypropyl(isothiazole-3-one hydrogen maleate salt. m.p. 224°-225°.

Claims to the invention follow.
What is claimed is:

1. Compounds having the formula

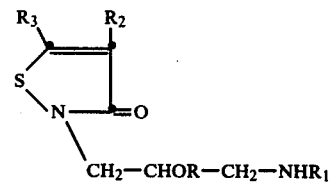

and pharmaceutically acceptable salts thereof, wherein R is hydrogen or C$_2$-C$_{12}$ acyl, R$_1$ is C$_1$-C$_{12}$ alkyl, R$_2$ is H, Cl, Br, F, CN, —NH$_2$, —COOR$_4$ wherein R$_4$ is H, C$_1$-C$_6$ alkyl, phenyl, biphenyl, naphthyl, or methyl substituted phenyl —CONR$_5$R$_6$ wherein R$_5$ and R$_6$, when separate, are H or C$_1$-C$_6$ alkyl and, when joined, are —CH$_2$—(CH$_2$)$_3$—CH$_2$—, —CH—CH$_2$—O—CH$_2$—CH$_2$—, —CH$_2$—CH$_2$—NH—CH$_2$—CH$_2$—, or —CH$_2$—CH$_2$—N(CH$_3$)—CH$_2$—CH$_2$—, —C$_1$-C$_6$ alkylthio, —C$_1$-C$_6$ alkylsulfinyl or —C$_1$-C$_6$ alkylsulfonyl and, R$_3$ is H, C$_1$-C$_6$ alkylthio, C$_1$-C$_6$ alkylsulfinyl or C$_1$-C$_6$ alkylsulfonyl.

2. Compounds of claim 1 wherein R$_3$ is H or —S—C$_1$-C$_6$ alkyl, r$_2$ is H, CN, Br, Cl or F and R is H.

3. Compounds of claim 2 wherein R$_3$ is —SCH$_3$, R$_2$ is CN and R$_1$ is —C(CH$_3$)$_3$.

* * * * *